United States Patent [19]
van Dijk

[11] Patent Number: 5,472,986
[45] Date of Patent: Dec. 5, 1995

[54] METHANOL PRODUCTION PROCESS USING A HIGH NITROGEN CONTENT SYNTHESIS GAS WITH A HYDROGEN RECYCLE

[75] Inventor: Christiaan P. van Dijk, Houston, Tex.

[73] Assignee: Starchem, Inc., Houston, Tex.

[21] Appl. No.: 336,298

[22] Filed: Nov. 8, 1994

[51] Int. Cl.⁶ .................................................. C07C 27/00
[52] U.S. Cl. ........................ 518/705; 518/703; 518/704
[58] Field of Search ................................ 518/704, 705, 518/703

[56] References Cited

U.S. PATENT DOCUMENTS

| | | | |
|---|---|---|---|
| 4,093,029 | 6/1978 | Weisz et al. | 518/705 |
| 4,181,675 | 1/1980 | Makin et al. | 518/705 |
| 4,650,814 | 3/1987 | Keller | 518/703 |
| 5,063,250 | 11/1991 | Murrayama et al. | 518/704 |
| 5,079,267 | 1/1992 | Kao et al. | 518/704 |
| 5,173,513 | 12/1992 | Pinto | 518/704 |
| 5,177,114 | 1/1993 | Van Dijk et al. | 518/703 |
| 5,245,110 | 9/1993 | Van Dijk et al. | 518/703 |

*Primary Examiner*—Werren B. Lone
*Attorney, Agent, or Firm*—Pravel, Hewitt, Kimball & Krieger

[57] ABSTRACT

A method for preparing methanol from a synthesis gas having less than 90% the stoichiometric amount of $H_2$ to convert the CO and $CO_2$ content of the synthesis gas to methanol by recycling into combination with such synthesis gas a sufficient amount of a hydrogen rich gas stream obtained as a permeate gas by diffusion of the process tail gas to provide a combined synthesis-recycle gas stream having at least about 95% of the stoichiometric amount of $H_2$ to convert its CO and $CO_2$ content to methanol. In a preferred embodiment of the invention compressed air is taken from a gas turbine to form the oxidant steam used in forming the synthesis gas, such synthesis gas in combination with the hydrogen rich recycle gas is processed through a series of methanol convertors to methanol and the non-permeate portion of the tail gas from this methanol process is returned as fuel to the gas turbine.

9 Claims, 1 Drawing Sheet

METHANOL PRODUCTION PROCESS USING A HIGH NITROGEN CONTENT SYNTHESIS GAS WITH A HYDROGEN RECYCLE

SPECIFICATION

1. Field of the Invention

This invention relates to a process for producing methanol from a synthesis gas produced by partial oxidation of natural gas with an oxidant steam having a high nitrogen content, such as air or an oxygen enriched air stream.

2. Background of the Invention

Methanol, in addition to being a commodity chemical, is potentially useful as a starting material in the production of hydrocarbon compounds useful as liquid fuels or organic compounds useful as octane boosters for liquid fuels, such as methyl t-butyl ether (MTBE). Methods for production of methanol have long been known and range from the early destructive distillation of wood to the more recent chemical methods of contacting a hydrogen ($H_2$) and carbon monoxide (CO) containing synthesis gas composition at high pressure, and more recently low pressure, with a catalyst composition that promotes the reaction of $H_2$ and CO to methanol.

Until recently, the chemical methods for catalytically preparing methanol from a synthesis gas have been too expensive to allow its use to make gasoline grade hydrocarbons that are competitive in cost with gasoline produced by refining of crude oil.

Conventional methods of synthesis gas formation were capitally intensive; steam reforming being expensive because of the energy input and equipment requirements and adiabatic reforming being expensive because of its need for an oxidant stream of low nitrogen content so as not to introduce inert species into the synthesis gas and also because of the need to perform a subsequent water-gas shift reaction and then a carbon dioxide ($CO_2$) removal process on the adiabatically formed synthesis gas to increase its $H_2$ content. The cost of either type of synthesis gas made the methanol produced therefrom too expensive to enable its use to produce gasoline that is economically competitive to that refined from crude oil. This, until recently, has been the case.

U.S. Pat. Nos. 5,177,114 and 5,245,110 to Van Dijk et al. describe methods by which methanol can be produced from natural gas at a greatly reduced cost compared to previous methods. Integral to these cost saving methods is the use of a gas turbine from which compressed air (21% $O_2$, 79% $N_2$) is taken to form the oxidant stream (either air or oxygen enriched air) for use in preparing a synthesis gas by adiabatic reforming—namely, partial oxidation—of methane. A synthesis gas prepared by partial oxidation—i.e., adiabatic reforming—is considerably more economical to prepare than one produced by steam reforming of methane. Further reducing the cost of producing the synthesis gas is the fact that air or an oxygen enriched air is used as the oxidant stream for the partial oxidation reaction rather than oxygen ($O_2$) such as would require production by a capitally expensive cryogenic $O_2$ separation unit. However, the use of air or an $O_2$ enriched air to produce the synthesis gas introduces into it a substantial quantity of nitrogen ($N_2$).

In the Van Dijk et al. method, this adiabatically formed synthesis gas of high $N_2$ content is then converted to methanol by sequential passage through a series of methanol conversion reactors. Conversion through a series of reactors, rather than by recycle-passthrough a single methanol conversion reactor, is required in the Van Dijk et al. method because the high $N_2$ content of the synthesis gas would make the recycle gas requirement for conversion through a single reactor prohibitively expensive. As produced, the methanol is recovered between stages or is left in the gas phase to be converted to other products such as gasoline which is then recovered, either procedure leaving as final gas composition, or "tail" gas, having a total heat of combustion BTU content and a BTU/scf heating value suitable for use as fuel for the gas turbine. All nitrogen introduced into the synthesis gas through the compressed air taken from the gas turbine to form the oxidant stream passes as an inert component through all product conversion process steps so that the entirety of this nitrogen becomes a component of the tail gas remaining after the final step of product recovery. Hence, if all tail gas can be utilized as fuel for the gas turbine, all nitrogen which was initially diverted from passage from the compressor side to the energy production unit or expander side of the gas turbine is ultimately returned to that unit in the tail gas fuel.

Since maintenance of a proper mass balance between the compressor side and the expander side (which includes the turbine combustion unit) of a gas turbine is critical to its proper operation and life expectancy, the ultimate return of all of this initially diverted nitrogen to the expander side of the gas turbine is a significant concern in the practice of Van Dijk et al. method. Unless this nitrogen is returned, the quantity of compressed air which may be taken from the compressor side of the gas turbine for use in forming a synthesis gas would be so limited as to be of no practical interest. Accordingly, it is of significant importance that substantially the entirety of the tail gas resulting after the final product recovery step be capable of use as fuel for the gas turbine. To the extent that a portion of the tail gas cannot be used as gas turbine fuel because the tail gas as a whole has too great a total heat of combustion BTU content or an inadequate BTU/scf heating value, to that extent a quantity of the nitrogen initially diverted from the expander side of the gas turbine is not returned to it and, accordingly, the quantity of compressed air that can be taken from the gas turbine for use in synthesis gas formulation is reduced. This then reduces the quantity of synthesis gas that can be produced which in turn increases the cost of production of the final product, especially as the capital cost obligations associated to the gas turbine contribute to final product cost.

One aspect of the methanol production method as described by the Van Dijk et al. U.S. Pat. Nos. 5,177,114 and 5,245,110 which is in need of improvement is that of the character of the synthesis gas. Production of methanol from a synthesis gas prepared by steam reforming has an advantage over that of a synthesis gas prepared by adiabatic reforming of methane. In a steam reformed synthesis gas—a typical composition of which is 15% CO, 8% $CO_2$, 74% $H_2$ and 3% $CH_4$—the quantity of $H_2$ in relationship to the content of CO and $CO_2$, expressed as a ratio of $(H_2)/(2CO+3CO_2)$ is at or above the stoichiometric value of 1.0 needed for complete conversion of all CO and $CO_2$ to methanol, typically being about 1.3–1.4. Such is not the case with respect to a synthesis gas prepared by adiabatic reformation wherein the value of this $H_2$ ratio is significantly less than 1.0, as on the order of about 0.8 to 0.85.

That the stoichiometric ratio of $H_2$ is less than 1.0 in an adiabatic reformation synthesis gas is in itself of no serious concern in the operation of the first or second reactors in a series of methanol conversion reactions. However, as the CO, $CO_2$ and $H_2$ content thereof is progressively reduced by conversion to methanol through a series of methanol conversion reactors the $H_2$ ratio of the remaining gas mixture progressively departs even more greatly from the ideal stoichiometric $H_2$ value, and this offers reasons for concern in terms of the life of methanol conversion catalyst exposed to the gas streams of progressively lesser stoichiometric $H_2$ value. Further, since the adiabatically formed syntheses gas is below the ideal stoichiometric $H_2$ value to start with, the quantity of methanol made over a given quantity of catalyst is less than could be achieved with a synthesis gas of ideal or greater stoichiometric $H_2$ ratio value. Also, the rate of conversion of an adiabatically produced synthesis gas is slower than when using a steam reformed synthesis gas of similar partial pressure of the reacting species.

It is therefor a desirable goal to develop a process for methanol production that produces a synthesis gas by adiabatic reformation, as by a method like that described in U.S. Pat. Nos. 5,177,114 and/or 5,245,110, which may be processed into methanol with the advantages that inure in the use of a synthesis gas having about or greater than the ideal stoichiometric value of $H_2$ as like that possessed by a steam reformed synthesis gas.

SUMMARY OF THE INVENTION

In its preferred embodiment this invention provides a method for processing natural gas into methanol by first converting natural gas by adiabatic reforming with use of an oxidant gas stream secured from compressed air taken from the compressor side of a gas turbine into a synthesis gas and combining that synthesis gas with a gas stream having a high content of hydrogen which is secured by diffusion of the process tail gas through a semipermeable membrane selective for the permeation of $H_2$ in comparison to $N_2$. The non-permeate portion of the tail gas has a total heat of combustion BTU content and a BTU/scf heating value which allows its use in its entirety as fuel for the gas turbine and is returned to the energy production unit of the expander side thereof as fuel. The hydrogen rich permeate is compressed and combined with the synthesis gas in a quantity sufficient to provide a combined synthesis-recycle gas stream having a $H_2$ ratio expressed as $(H_2)/(2CO+3CO_2)$ which is about or greater than 1.0.

As one advantage, this invention eliminates concerns that operations with a sub-stoichiometric synthesis gases may cause with respect to the life expectancy of the methanol conversion catalyst. Another advantage of this invention is that it provides a synthesis-recycle gas of richer concentration in the molecular species that are reactive to produce methanol (i.e., $H_2$, CO and $CO_2$), hence the synthesis-recycle gas allows for use of a lesser quantity of methanol conversion catalyst for an equivalent amount of methanol produced than would be required for processing the sub-stoichiometric synthesis gas under similar reaction conditions of temperature and pressure.

DESCRIPTION OF THE PREFERRED EMBODIMENTS

Figure 1:
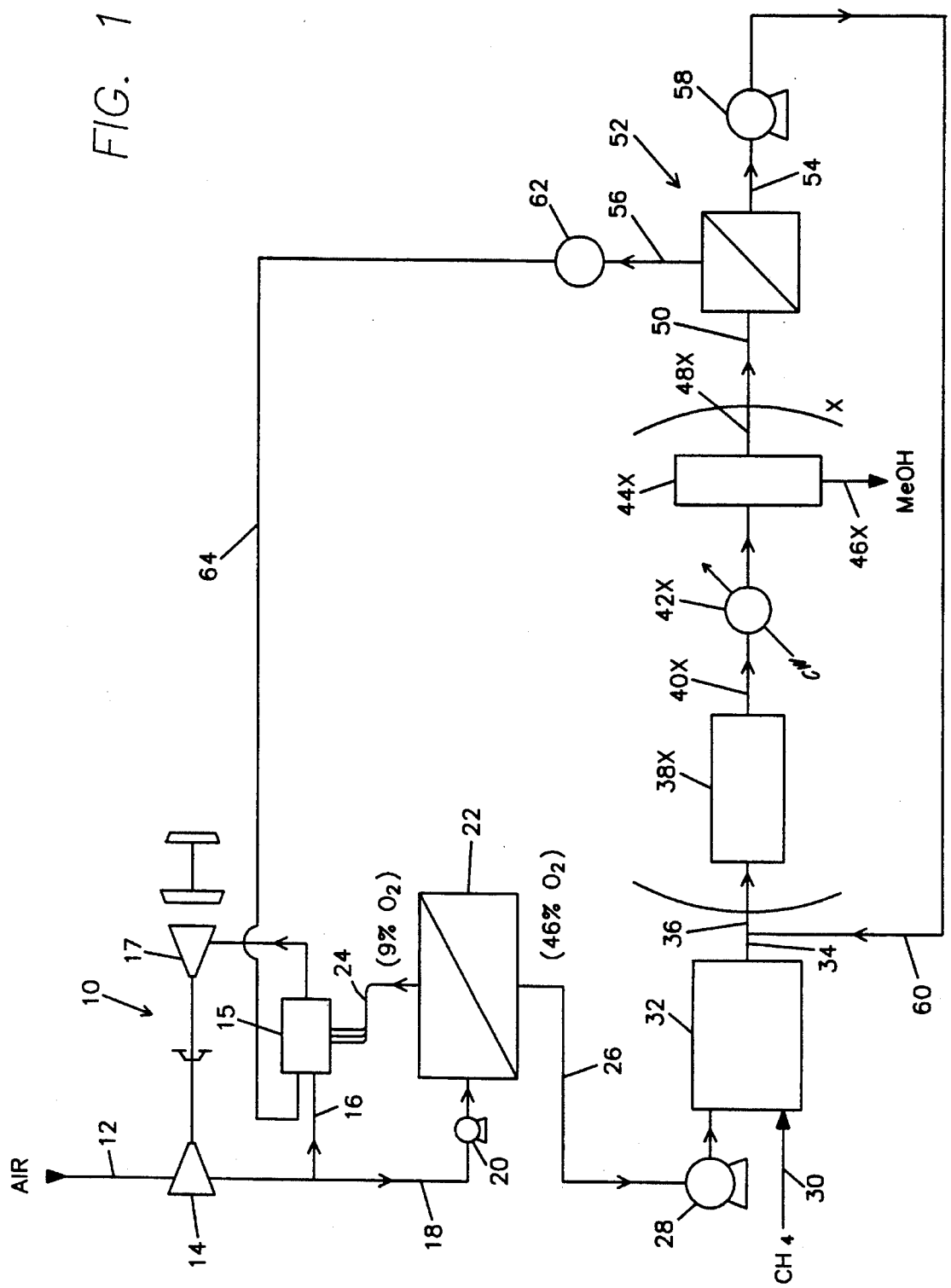
FIG. 1 schematically illustrates a process embodiment of the invention wherein a hydrogen rich gas stream is obtained as a permeate gas stream by diffusion from the process tail gas and is recompressed and recycled into admixture with a synthesis gas formed by partial oxidation of natural gas with an oxidant stream secured from compressed air taken from a gas turbine, with the non-permeate portion of the tail gas returned as fuel to the gas turbine.

The invention comprises a method for converting a sub-stoichiometric synthesis gas—i.e., one in which the $H_2$ content is stoichiometrically insufficient for conversion of its CO and $CO_2$ content—into methanol with all advantages inherent in the conversion of a stoichiometrically correct synthesis gas. The synthesis gas may be prepared by adiabatic reforming with an oxidant gas stream secured from any source, such as oxygen from a cryogenic $O_2$ separation unit or compressed air or $O_2$ enriched air produced by use of conventional compressors to diffuse air through a membrane unit or process in a swing-pressure-absorption unit. However, because of the cost advantages of the process as described in U.S. Pat. Nos. 4,177,114 and 5,245,110 to Van Dijk et al., it is preferred to form the synthesis gas by these methods, using an oxidant gas stream which is secured from compressed air taken from a gas turbine that is integral to the methanol production process. To more effectively utilize the process as described by these patents, according to the present invention, the tail gas remaining after the final step of product recovery is diffused through a membrane which is preferential for permeation of $H_2$ over $N_2$ and the $H_2$ rich permeate is compressed and combined with a synthesis gas prepared by adiabatic reforming of natural gas in a quantity sufficient to provide a combined synthesis-recycle gas stream having a $H_2$ content that is about or above the stoichiometric $H_2$ amount required for conversion of its CO and $CO_2$ content to methanol. The non-permeate portion of the tail gas is used as fuel for a gas turbine from which compressed air is taken to form the oxidant gas stream used to adiabatically react natural gas to the synthesis gas utilized in the process. Operation of the gas turbine within the limits of its requirements for mass balance between its compressor side and expander side is thus maintained by returning to the energy production unit of the expander side of the turbine substantially all nitrogen that was initially diverted in the compressed air taken from its compressor side for synthesis gas formation. This nitrogen passes through the methanol production process to become part of the non-permeate tail gas used as fuel for the gas turbine.

The preferred use of the gas turbine, as in U.S. Pat. Nos. 5,177,114 and 5,245,110, is to extract as large an amount as possible of compressed air out of the compressor side of the gas turbines, cool this air, compress it somewhat further as may be necessary and then pass this air over a semipermeable surface with a preference for diffusion of oxygen, so as to obtain low pressure $O_2$ enriched air by diffusion. This $O_2$ enriched air is then compressed and used for adiabatic reforming of pressurized natural gas. In this way a synthesis gas is obtained which contains all the nitrogen that was co-diffused with the oxygen. After a series of reaction steps over methanol catalysts and recovery of methanol by cooling the reaction gases, the final tail gas is fed back to the gas turbine as fuel. It is preferred that all of this tail gas be used as fuel because in this manner all of the co-diffused nitrogen is ultimately fed back to the expander side of the gas turbine.

It is also necessary that on combustion of this final tail gas that the correct amount of heat be produced to drive the gas turbine(s) in the system. Small variations in this heat can be tolerated, but large variations cannot be accepted.

In the first instance the fuel to a gas turbine, this being the final tail gas, has to provide the energy for warming up the compressed feed to the expander so that the expansion provides more energy than the compression of the air has cost. In normal gas turbine operation the fuel feed is controlled, so that the correct BTU content is fed. Too much fuel feed—i.e., too great a heat of combustion BTU content—is especially harmful. In that case the temperature of the hot combustion gases, as fed to the expander, can be higher than allowed for the quality of the metal in the expander. For every gas turbine a maximum so-called turbine inlet temperature (TIT) is given as a maximum operating constraint. Control of this temperature is carried out by monitoring the temperature of the expanded gases. While too much fuel can be disastrous, the contrary—too little fuel—is also not attractive. The amount of energy (as horsepower) produced by a gas turbine is in first approximation directly proportional to the heat provided by the fuel. Less fuel than allowable under the BTU/horsepower rating of the turbine results in lower than maximum energy output by the gas turbine.

In using a gas turbine operation for the methanol process as described in the Van Dijk et al. patents, another aspect comes to the fore. In extracting compressed air from the gas turbine and subjecting that stream to diffusion through a semipermeable wall, enriched air is obtained, which therefore contains in addition to the oxygen used in the methanol process, a considerable amount of co-diffused nitrogen, which is also then diverted from passage to the expander side of the gas turbine. However, in finally bringing the tail gas out of the methanol process back to the gas turbine as fuel, practically all of the co-diffused nitrogen is added back to the expander side of the gas turbine. This effectively reduces the loss of expander mass flow and energy considerably.

It is therefore highly preferred in proper operation of the methanol process as described in the Van Dijk et al. patents to use practically all of the final tail gas as fuel to the gas turbine(s). As a first approximation this then defines the total heat of combustion (total BTU content) that the tail gas fuel stream can contain. Slight aberrations from this value can be compensated for by changes in the temperature of preheat of the tail gas fuel and the compressed air, (denuded of some of its oxygen) which is fed to the expander side of the turbine. But in a first approximation the total lower heating value (LHV) of the tail gas is a given, defined by the desired amount of energy that the gas turbine system has to provide for the process. This total desired energy can encompass also electrical energy that the plant has to use, next to the direct needs for compression shaft horsepower.

Whatever its make or model, each gas turbine has a maximum horsepower (hp) output rating which cannot be exceeded without adverse effect on the gas turbine. Further, each gas turbine has a BTU/hp energy rating profile the particular value of which varies slightly as a function of the ambient air temperature of the environment within which the gas turbine operates. Still further, in terms of the mass flow through the turbine compressor side as air being compressed therein and combustion gases expanding through the turbine expander side to produce horsepower, any difference in mass flow therebetween must not exceed the design of the gas turbine thrust bearing which, under typical designs, provides for a maximum of 10% greater mass flow through the expander side than that flowing through the compressor side. Hence, as an illustration, a GE Frame 5 Gas Turbine has a maximum horsepower output rating of about 36,000 hp and, at moderate ambient air temperatures, an energy rating of about 7949.3 BTU/hr. Thus, for maximum horsepower output operations the GE Frame 5 Gas Turbine operates at its maximum rated output when fueled with a feed that provides 286,174,800 BTU/hr to provide 36,000 hp/hr. If fed with a fuel that provides a significantly greater than 286,174,800 BTU/hr quantity of heat, the Turbine-inlet-Temperature (TIT) would be exceeded and the turbine would be adversely affected. This maximum heat quantity of fuel feed can be modestly exceeded—say, by about 5%—and the excess accommodated through otherwise modifying the temperature of the compressed gas-fuel feed to the expander side of the turbine.

Accordingly, using a GE Frame 5 Gas Turbine for illustration, the tail gas resulting from a methanol production process as described by the Van Dijk et al. patents which is utilized as fuel for a GE Frame 5 Gas Turbine desirably should not exceed 1.05 times a heating value of 286,174,800 BTU/hr when the gas turbine is operating under moderate temperature conditions. To achieve this goal in the Van Dijk et al. process the synthesis gas must be processed under conditions of temperature and pressure with a quantity of methanol conversion catalyst and through a number of methanol conversion stages sufficient to deplete its CO and $H_2$ content by conversion to recovered methanol product such that the final gas remaining after product recovery has a heat of combustion BTU content (or a LHV) no greater than this maximum value.

Reduction of the LHV of the reacting gas stream to the desired value takes place in the methanol process by conversion of the initial nitrogen-containing synthesis gas into methanol, according to the equations:

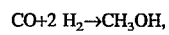

$$CO+2\ H_2 \rightarrow CH_3OH,$$

and

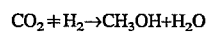

$$CO_2 + H_2 \rightarrow CH_3OH + H_2O$$

This discussion so far therefore stresses the desirability of deep conversion of the nitrogen-containing synthesis gas. There is, however, also a limit on this conversion level. Most gas turbines have lower limits on the amount of heating value per cubic foot of fuel gas.

There are actually three zones of fuel contents. For general use the fuel with the highest heating value is natural gas, which has, depending on its composition, fuel values of around 900 to 1000 BTU/scf. Other gaseous fuels may have less heating value, down to 300 to 500 BTU/scf, and these can be treated in a somewhat similar manner as natural gas. When, however, the heating value falls below this level of about 300 BTU/scf, a rigorous inspection of gas turbine conditions is called for, this to avoid feeding too much inert material to the expander side. The next zone concerns gases with heating values of around 100 BTU/scf. At this low value it becomes necessary to determine if the fuel gas can be completely burned in the residence time in the burner or burners of the gas turbine before entering the expander proper. Incomplete combustion can easily lead to deposition of carbonaceous material on the expander blades, which will lead to an early demise of the gas turbine involved.

It is then essential that the heating value of the tail gas fuel not be too low, preferably it should be at least about 100 BTU/scf, but lower value gaseous fuels have been run occasionally with success. Also, such low BTU/scf fuel gases should have fast burning characteristics. This is especially true when the available burner space of the gas turbine is limited, which in a relatively large number of commercially available gas turbines is indeed the case.

The fastest burning material is hydrogen. A considerable fraction of the heating value of such fuel gas with very low hearing value has to be provided by hydrogen. A reasonable fraction is about 30 to 40% as a minimum of the heat of combustion BTU content is supplied by hydrogen. The fast burning hydrogen elevates the temperature of the flame considerably in relatively little space, whereupon the other combustibles of the low heating value fuel have more chance to be burned properly. Especially when hydrogen has been burned already, and the gas temperature has therefore been increased and hot steam has become available, any CO present in the tail gas fuel will then burn with great speed.

Any methane present burns slow. It is essential that the temperature be really elevated so that this slow burning species can be totally converted into $CO_2$. It is therefore not attractive to have more than say 30% of total heat of combustion content available as methane in the tail gas fuel.

These conditions translate to the necessity of a given conversion of the synthesis gas, this as stated to feed to the gas turbines all the final tail gas without overloading the gas turbines with production of too much heat. This necessity leads in the process of the Van Dijk et al. patents to either a choice of a high pressure reaction in order for the methanol reaction to proceed to the desired degree of conversion by the final methanol reactor stage, or to a larger number of methanol reaction stages, or a combination of these two requirements.

The process of this invention provides for conditioning an adiabatically produced synthesis gas with additional hydrogen taken as a recycle stream obtained by diffusion from the process tail gas to make the combined synthesis-recycle gas stream more readily convertible to recovered methanol to the degree of conversion desired to provide a process tail gas the non-diffused portion of which has a heat of combustion BTU content and a BTU/scf heating value that allows its entire use as turbine fuel. With the process of this invention the requisite amount of methanol needed to be produced and recovered from the synthesis-recycle gas stream to provide the desired tail gas derived fuel stream for the gas turbine is produced under less stringent constraints of temperature and pressure and with a lesser quantity of methanol catalyst and/or fewer methanol conversion steps than would be otherwise required. Further, with the process of the invention the possibility of premature aging and/or damage occurring to the methanol catalyst, both in the early and in the latter methanol production stages, is reduced.

With the process or this invention, natural gas may be converted to methanol or other products derived from methanol by the treatment of an adiabatically formed synthesis gas through a series of conversion reactors with all advantages as if the synthesis gas was ideally balanced with respect to the stoichiometric quantity of $H_2$ required for conversion of its CO and $CO_2$ content to methanol. The synthesis gas is prepared with an oxidant gas stream secured from compressed air taken from the compressor side of a gas turbine. The quantity of synthesis gas that can be so formed while maintaining the gas turbine within its requirements for mass balance between its compressor and expander sides is maximized by ultimate return to the expander side of the gas turbine of all nitrogen initially diverted therefrom by the taking of compressed air from the compressor side for utilization in the production of the adiabatically formed synthesis gas. Accordingly, the tail gas remaining after the final stage of product recovery is diffused through a membrane preferential for the permeation of Hz relative to $N_2$ and the $H_2$ rich permeate is compressed and recycled into combination with the synthesis gas to enrich its $H_2$ content to about or in excess of the stoichiometric quantity of $H_2$ required to convert the CO and $CO_2$ content of the combined synthesis-recycle gas stream to methanol and the non-permeate tail gas stream is employed as the fuel for the gas turbine.

The number of methanol conversion reactors through which the synthesis and $H_2$ rich recycle gas are processed and the conditions of their operation are selected to achieve a conversion of the $H_2$, CO and $CO_2$ content of the combined synthesis and $H_2$ rich recycle gas that provides a final tail gas composition the non-permeate portion of which can be utilized in its entirety as fuel feed to the energy production unit of the expander side of the gas turbine, thus returning to it all nitrogen initially diverted from it by inclusion in the compressed air taken from the gas turbine's compressor side for use in forming the synthesis gas.

FIG. 1 illustrates an embodiment of the present invention which utilizes a series of multiple methanol conversion reactors with interstage recovery of methanol. A gas turbine 10 is integral to the process in that air 12 compressed in compressor side 14 is split after compression into compressed air streams 16 and 18 and compressed air stream 18 is further compressed, if necessary, by compressor 20 and then fed to a membrane diffusion unit which preferentially diffuses oxygen in preference to nitrogen. An oxygen rich permeate gas stream 26 and an oxygen depleted, or nitrogen rich, non-permeate gas stream 24 are formed. The non-permeate nitrogen rich gas stream 24 and the other portion of the initially compressed air 16 are fed to the combustion unit 15 of expander side 17 of the gas turbine where ultimately they combine with fuel fed to this unit to power the gas turbine 10. The oxygen-rich permeate gas stream 26 is compressed in compressor 28 and then passed into an adiabatic reformer reactor 32 into which pressurized natural gas 30 is also passed. There the natural gas is partially oxidized—i.e., adiabatically reformed—to produce a synthesis gas containing CO, $CO_2$, $H_2$ and other components wherein the ratio of $(H_2)/(2\,CO+3CO_2)$ is about or less than 0.85. Preferably, water is first condensed and removed from this synthesis gas 34 (not shown) and thereafter it is combined with a hydrogen rich recycle gas stream supplied by line 60. The hydrogen rich gas stream 60 is supplied in an amount that upon its combination with the synthesis gas 34 forms a combined synthesis-hydrogen recycle gas stream 36 wherein the ratio of $(H_2)/(2\,CO+CO_2)$ is at least about 0.95, and preferably 1.0 or greater. This combined synthesis-hydrogen recycle gas stream is then fed to the first of a plurality (x) of methanol conversion reactors 38x wherein the gas contacts a methanol conversion catalyst to react a portion of the $H_2$, CO and $CO_2$ content of the gas to methanol. Following the reaction the effluent gas 40x from methanol reactor 38x is cooled by a chill water heat exchanger 42x and passed to separator 44x wherein a liquid phase 46x of methanol and water is separated from the remainder of the synthesis-hydrogen recycle gas stream 48x. The remainder of the synthesis-hydrogen recycle gas stream is then reheated (not shown) and passed to the next in series of the plurality of methanol conversion reactors wherein the process of conversion to methanol and methanol-water removal and the remainder of the synthesis-hydrogen recycle gas stream reheat for feed to the next methanol reactor, as described above for the first reactor, is repeated. This stepwise processing is repeated until the synthesis-hydrogen recycle gas stream has passed through all of the x number of methanol reactors of the series—as indicated by the parenthetical repeating units of the figure. Following methanol and water removal from the effluent gas 48x of the last methanol reactor, the remainder of the gas stream, that is, the process "tail gas" 50 is passed to a membrane diffusion unit 52 which is preferential for the diffusion of $H_2$ compared to $N_2$ to form a hydrogen rich permeate gas stream 54 which is recompressed by compressor 58 and fed by line 60 into combination with synthesis gas 34. The non-permeate portion of the tail gas stream 56 is heat exchanged in heat exchanger 62 and fed by line 64 as fuel to the combustion unit 15 of the expander side 17 of the gas turbine 10.

Many types of membrane materials are known in the art which are highly preferential for diffusion of hydrogen compared to nitrogen. Such membrane materials include those composed of silicon rubber, butyl rubber, polycarbonate, poly(phenylene oxide), nylon 6,6, polystyrenes, polysulfones, polyamides, polyimides, polyethers, polyarylene oxides, polyurethanes, polyesters, and the like. In the process of this invention the membrane material selected is preferably also highly preferential for diffusion of hydrogen compared to carbon dioxide, although this preference is by no means critical to the practice of this invention. Accordingly, membrane materials like those discussed in U.S. Pat. No. 4,181,675 which also provided for significant codiffusion of $CO_2$ may also be readily utilized in this invention. The membrane units may be of any conventional construction, and a hollow fiber type construction is preferred.

As may be more readily seen for an examination of the examples which follow, essentially the $H_2$ enriched permeate gas stream used as recycle is merely borrowed temporarily to provide for a processing of the sub-stoichiometric synthesis gas into methanol with the ease that would be inherent in the processing of a synthesis gas which was of an ideal stoichiometric $H_2$ ratio. But, since the $H_2$ rich permeate gas is a recycle gas stream operation, it in effect does not otherwise become a significant part of the methanol conversion process since it is recovered after the final product conversion step as a gas stream for recycle use.

In further illustration of the invention, two examples are provided, one of practice of the invention and the other is a comparative example of the results of treatment of a similar beginning synthesis gas without benefit of the invention. Feed and product gas compositions are given in 1$b$-moles/hour, denoted as MPH, pressures are in terms of absolute atmospheres, denoted as ata.

EXAMPLES

Example No. 1

A feed gas, containing 36064.18 MPH methane, 757.58 MPH ethane, 357.64 MPH $CO_2$, and 26.64 MPH $N_z$ is mixed with 45095.20 MPH steam, warmed up to 950° F. and reacted with 48888.8 MPH ata 48 mole % oxygen-containing enriched air, preheated to 850° F. The combined gas stream is reacted over a reforming catalyst to produce a synthesis gas having an exit temperature of 1990° F. This synthesis gas contains 27886.19 MPH CO, 70230.80 MPH $H_2$, 8923.41 MPH $CO_2$, 47010.74 MPH $H_2O$, 1127.38 $CH_4$, and 25448.82 MPH $N_2$ and is at a pressure of 74.2 ata. This synthesis gas has a $H_2$ ratio, expressed as $(H_2)/(2 CO + CO_2)$, of 0.851. After cooling and removal of condensed water the synthesis gas is combined with a hydrogen-containing recycle gas stream, obtained by diffusion out of the tail gas remaining after the methanol conversion and recovery steps. The composition of the hydrogen-containing recycle gas stream is approximately 348.08 MPH CO, 26000.88 MPH $H_2$, 4628.29 MPH $CO_2$, 39.58 MPH $CH_4$, 1230.75 MPH $N_2$, and approximately 300 MPH methanol.

This combined synthesis-recycle gas mixture, which has a $H_2$ ratio of 0.991, is contacted with a methanol conversion catalyst in five methanol reactors under heat removal, producing methanol by reaction of the CO and $CO_2$ with hydrogen. The pressure of the combined synthesis-recycle gas stream as feed to the first methanol reactor is 72.7 ata. To insure against overheating of the catalyst in this and later reactions the catalyst is indirectly cooled by boiling water in close proximity to the catalyst, thus a reaction temperature of about 500° F. is maintained. The exit gases are in-between reactions and after the last reactor cooled to condense and remove water and most of the methanol made.

The effluent gas of the first reactor contains 19304.56 MPH CO, 76901.38 MPH $H_2$, 13061.4 MPH $CO_2$, 884.5 MPH $H_2O$, 1166.96 MPH $CH_4$, 26679.57 MPH $N_2$, and 9720 MPH CHaOH. At the exit pressure of 71.4 ata the pseudo reaction constant is obtained as the product of partial pressure of CO and the square of the partial pressure of hydrogen, divided by the partial pressure of methanol. The constant then is 2744, a value corresponding to a very high reaction temperature of circa 550° F. instead of the actual temperature of about 500° F., thus indicating a large driving force for reaction. On cooling of this first reactor effluent gas, 9118.9 MPH methanol and about 884.5 MPH water are condensed and recovered and the gas stream remaining is fed to the next methanol reactor.

Similarly the reaction in the second methanol reactor is carried out with a pseudo reaction constant of 1350, while in the next three methanol reactors this value is taken at 1300, 1250 and 1800. The last high value is to limit conversion to the desired level. Between each stage the effluent gas is cooled, water and most of the methanol are condensed and recovered and the remainder of the gas stream is fed to the next methanol reactor. A pressure drop between each reactor of about 1.3 to 1.5 ata occurs. After removal of the last amount of methanol a gas stream is obtained at 64.6 ata and is of the composition: 4652.7 MPH CO, 34123.24 MPH $H_2$, 8576.6 MPH $CO_2$, approximately 1166.96 MPH $CH_4$, and approximately 26679.57 MPH $N_2$, together with an uncondensed amount of methanol of 370 MPH.

The $H_2$ stoichiometry factor, earlier defined as $(H_2)/(2CO+3CO_2)$, is for the different reactor effluents respectively, 0.9885, 0.9848, 0.9811, 0.9773 and 0.9745. These values are close enough to the stoichiometrical ideal of 1.00 to be acceptable for performance. If desired, a slightly larger hydrogen recycle stream will, of course, further increase the $H_2$ stoichiometry value to 1.00 or more.

By combining the different condensates a raw methanol stream is obtained containing approximately 28496.67 MPH methanol and 5369.3 MPH water.

By diffusion the gas stream remaining after the last step of methanol recovery through a membrane the hydrogen-rich recycle stream mentioned above is obtained as a permeate gas stream at a pressure of about 125 psia (about 8.5 ata). This stream is then compressed to 72.7 ata and recycled into combination with a fresh feed of synthesis gas as has been discussed.

The final remaining non-permeate tail gas stream contains 4294.62 MPH CO, 8122.37 MPH $H_2$, 3948.31 MPH $CO_2$, approximately 1127.38 MPH methane and 25448.82 MPH nitrogen, together with a remaining methanol amount of 70 MPH. This stream which is at about 63 ata is proportioned as feed and fed to an array of six GE Frame-5 gas turbines. The heating content of the non-permeate tail gas stream is approximately $17.78 \times 10^8$ BTU/Hr, an amount sufficient to keep the six gas turbines operating properly. Also the heating value of this non-permeate tail gas stream per scf is about 109 BTU, which is acceptable, taking into account the hydrogen content of this stream. That is, each of the six gas turbines receives as its fuel feed a one-sixth portion of the non-permeate tail gas, which portion contains 296,333,333

BTU/hr of heating content. Likewise, compressed air from each turbine is diffused through a membrane preferential to the diffusion of $O_2$ compared to $N_2$ and each provides a one-sixth portion of the 48 mole % $O_2$ enriched air stream used as the oxidant gas stream in a quantity of 48,888.8 MPH to form the synthesis gas.

Example No. 2 (Comparative)

A synthesis gas of an identical composition as that in Example No. 1 is formed, cooled to condense and remove water, then at a pressure of 72.7 ata is fed to the first of a series of five methanol conversion reactors. Each of the methanol conversion reactors is operated under the same conditions of catalyst quantity and of gas inlet and outlet temperature as in Example No. 1 and the effluent gas from each is cooled to condense and remove water and most of the methanol therefrom before the remainder of the gas stream is fed to the next methanol reactor in the series. A pressure drop between reactors of about 1.3 ata occurs.

The pseudo reaction constant for the conversion obtained in each of the reactors is, respectively, 2744, 1350, 1300, 1250 and 1800 and the $H_2$ stoichiometry factor defined as the ratio of $(H_2)/(2CO+CO_2)$ of the synthesis gas initially and of the effluent gas of each reactor is, respectively, 0.8508, 0.8155, 0.7604, 0.7086, 0.6616 and 0.6312. Total methanol make and recovery, together with co-recovery of water, is $CH_3OH$ 23,287.43 MPH and $H_2O$ 2,141.4 MPH. The composition of the tail gas stream remaining after the methanol and water recovery steps in MPH is CO 6,042.4, $H_2$ 21,071.8, $CO_2$ 7,099.6, $CH_4$ 1,127,4, $N_2$ 25,448.8 and $CH_3OH$ 280.2 This tail gas stream has a pressure of 65.4 ata, a heating content of $33.993 \times 10^8$ BTU/hr and a heating value of 147 BTU/scf.

The heating content of this tail gas is about twice that amount which is permissible as fuel feed to an array of six GE Frame 5 gas turbines. Even in a mode of maximum rated operation of each turbine, as like the case in Example No. 1, only 12,086,888 scf (about 53.3 vol. %) of this tail gas can be utilized as gas turbine fuel, meaning that 11,024,208 scf (about 47.7 vol. %) can not be used as fuel. This being the case, the gas turbines could not in the first instance be operated in a manner to produce 48,888.8 MPH of a 48 mole % $O_2$ enriched air by diffusion of compressed air from these gas turbines because this amount of $O_2$ enriched air production would place the turbines in violation of their mass balance design constraint since 47.7 volume % of the tail gas with its $N_2$ and other mass components cannot be returned to the expander side of the turbine to balance the mass lost therefrom in the $O_2$ enriched air. This, in turn, means that the quantity of synthesis gas proposed for use in Example No. 2 cannot be produced in a process arrangement of five methanol reactors integrated with six GE Frame 5 gas turbines as is utilized in Example No. 1.

In effect, in Example No. 2, the level of conversion by the completion of the fifth methanol reaction is not sufficient to permit full utilization of the six gas turbines and either more methanol reactors would be required or conditions of temperature and/or pressure would have to be changed to higher extremes favorable to a greater degree of conversion in the five methanol reactors used. This, however, may place the methanol catalyst in even greater jeopardy of premature aging or destruction than that which the use of a substoichiometric synthesis gas may otherwise impose under less severe conditions of temperature and pressure for the methanol reaction.

Although the invention has been described with reference to its preferred embodiments, from this description those skilled in the art may appreciate changes and modifications thereto which do not depart from the scope and spirit of the invention as described herein and claimed hereafter.

I claim:

1. A process for converting natural gas to methanol or products derivative of methanol, comprising the steps of:
    partially oxidizing natural gas with an oxidant stream to form a synthesis gas containing $H_2$, CO and $CO_2$ in a ratio of $(H_2)/(2CO+3CO_2)$ less than 1.0;
    combining the synthesis gas with a hydrogen rich recycle gas stream secured as a permeate gas stream from diffusion of a tail gas stream remaining after completion of methanol recovery through a semipermeable membrane preferential for permeation of $H_2$ in preference to $N_2$, said hydrogen rich recycle gas stream being used in an amount that provides a combined synthesis-recycle gas stream containing $H_2$, CO and $CO_2$ in a ratio of $(H_2)/(2CO+3CO_2)$ which is greater than that of the synthesis gas;
    passing said combined synthesis-recycle gas stream into a plurality of contacts with a methanol conversion catalyst with recovery of methanol from said gas stream between contacts with a methanol conversion catalyst to form after the last methanol recovery step a tail gas stream from which the hydrogen rich recycle gas stream is secured by diffusion.

2. The process of claim 1, wherein said synthesis gas has a ratio of $(H_2)/(2CO+3CO_2)$ of 0.85 or less.

3. The process of claim 2, wherein the combined synthesis-recycle gas stream has a ratio of $(H_2)/(2 CO+CO_2)$ of 0.95 or greater.

4. The process of claim 3, wherein the combined synthesis-recycle gas stream is passed into at least three contacts with a methanol conversion catalyst.

5. The process of claim 4, wherein the oxidant stream is secured from compressed air taken from a gas turbine and the non-permeate portion of the tail gas following recovery of the hydrogen rich recycle gas stream is utilized as fuel for the gas turbine.

6. The process of claim 5, wherein the non-permeate portion of the tail gas has a heating value of 100 BTU/scf or greater.

7. The process of claim 6, wherein the non-permeate portion of the tail gas is used in its entirety as gas turbine fuel.

8. The process of claim 6, wherein the non-permeate portion of the tail gas has at least 30% of its heat of combustion content supplied by hydrogen.

9. The process of claim 8, wherein no more than 30% of the heat of combustion content of the non-permeate portion of the tail gas is supplied by a hydrocarbon.

* * * * *